(12) United States Patent
Wang

(10) Patent No.: US 11,376,342 B2
(45) Date of Patent: Jul. 5, 2022

(54) MINIATURE AROMATHERAPY DIFFUSER

(71) Applicant: Xiaoming Wang, Shanghai (CN)

(72) Inventor: Xiaoming Wang, Shanghai (CN)

( * ) Notice: Subject to any disclaimer, the term of this patent is extended or adjusted under 35 U.S.C. 154(b) by 251 days.

(21) Appl. No.: 16/624,007

(22) PCT Filed: Jan. 29, 2019

(86) PCT No.: PCT/CN2019/073559
§ 371 (c)(1),
(2) Date: Dec. 18, 2019

(87) PCT Pub. No.: WO2020/143087
PCT Pub. Date: Jul. 16, 2020

(65) Prior Publication Data
US 2021/0338875 A1 Nov. 4, 2021

(30) Foreign Application Priority Data
Jan. 11, 2019 (CN) .......................... 201920051129.3

(51) Int. Cl.
*A61L 9/03* (2006.01)
*H01R 35/04* (2006.01)
*H01R 103/00* (2006.01)

(52) U.S. Cl.
CPC .............. *A61L 9/037* (2013.01); *H01R 35/04* (2013.01); *A61L 2209/133* (2013.01); *H01R 2103/00* (2013.01)

(58) Field of Classification Search
CPC .... A61L 9/037; A61L 2209/133; H01R 35/04
See application file for complete search history.

(56) References Cited

U.S. PATENT DOCUMENTS

| | | | | |
|---|---|---|---|---|
| 5,352,122 A * | 10/1994 | Speyer | .................... | F21S 8/035 439/13 |
| 6,862,403 B2 * | 3/2005 | Pedrotti | .................. | A61L 9/037 392/395 |
| 7,932,482 B2 * | 4/2011 | Norwood | ............ | A01M 1/2077 219/506 |
| 2006/0193610 A1 * | 8/2006 | Han | .......................... | A61L 9/03 392/390 |

* cited by examiner

*Primary Examiner* — Timothy C Cleveland
(74) *Attorney, Agent, or Firm* — Bayramoglu Law Offices LLC

(57) ABSTRACT

The miniature aromatherapy diffuser comprises a main shell and a perfume bottle assembly, a heating body fixed seat is arranged in the main shell, one end of the heating body fixing seat is provided with a connecting cavity, and the other end is detachably assembled with a heating body; a PCB assembly is arranged on the heating body fixing seat, and both sides of the heating body are provided with electrodes connected with the PCB assembly. The perfume bottle assembly comprises a bottle body and a cotton bar, the bottle body is connected with the connecting cavity, one end of the cotton bar extends out of the mouth of the bottle body and extends into the heating body; a fragrance emitting area is arranged on the main shell, and the main shell is also provided with a rotary plug socket.

11 Claims, 7 Drawing Sheets

MINIATURE AROMATHERAPY DIFFUSER

CROSS REFERENCE TO THE RELATED APPLICATIONS

This application is the national phase entry of International Application No. PCT/CN2019/073559, filed on Jan. 29, 2019, which is based upon and claims priority to Chinese Patent Application No. CN201920051129.3, filed on Jan. 11, 2019, the entire contents of which are incorporated herein by reference.

TECHNICAL FIELD

The invention belongs to the technical field of aromatherapy diffuser. To be specific, it is a miniature aromatherapy diffuser.

BACKGROUND

Since the Reform and Opening Up, aromatherapy has become popular in many cities thanks to enriched material life and improved quality of life. Popular aromatherapy methods in some cities today include aromatherapy skincare, aromatherapy treatment and home fragrance. In general, aromatherapy costs are high, making it exclusive to the middle to high income group. Therefore, many see aromatherapy as an imported luxurious lifestyle, a symbol of quality life.

Aromatherapy is popular with women who pursue beauty in their lives around the world. It nourishes skin and reduces stress. Essential oils are absorbed by human blood and lymph through massage, inhalation, hot compress, tub bathing, and steaming, which increases metabolism, boosts cell regeneration, improve immunity, and as a result, regulate the nervous system, circulatory system, endocrine system, muscle tissues, digestive system and excretory system. Regular aromatherapy bathing and massage with soft music gives sweet floral fragrance to the nose and makes one charming and romantic.

Existing aromatherapy diffusers are generally simple in structure and have the following defects.

(1) Most devices have non-detachable plugs. Users may have difficulty connecting it to the socket due to the socket direction. The perfume is thus likely to flow out as well.

(2) Existing diffusers usually use cement resistance for heating, which is not compatible with wide-range voltage. Changes of voltage lead to temperature instability.

(3) Most devices use screw connection which results in low assembly efficiency and is not conducive to automatic production;

(4) Specifications of the plug are fixed and difficult to replace, making it difficult to change the plug by country.

(5) Most devices use leads for internal connection, which is not conducive to automatic production and leads to low capacity.

SUMMARY

In view of the above, in order to solve existing technical problems, the invention provides a miniature aromatherapy diffuser solution.

The technical scheme adopted by the invention is as follows: a miniature aromatherapy diffuser, which comprises a main shell and a perfume bottle assembly with hollow structures, a heating body fixed seat is arranged in the main shell, one end of the heating body fixing seat is provided with a connecting cavity, and the other end is detachably assembled with a heating body; a Printed Circuit Board (PCB) assembly is arranged on the heating body fixing seat, and both sides of the heating body are provided with electrodes connected with the PCB assembly. The perfume bottle assembly comprises a bottle body and a cotton bar, the bottle body is connected with the connecting cavity, one end of the cotton bar extends into the bottle body, the other end extends out of the bottle mouth of the bottle body, and extends into the heating body; a fragrance emitting area is arranged on the main shell, and the main shell is also provided with a rotary plug socket; a conductive copper sheet is arranged in the main shell, and one end of the conductive copper sheet is connected with the rotary plug socket, and the other end is connected with the PCB assembly.

Further, a bottle stopper is sleeved outside the cotton bar, and the bottle stopper is fixed in the mouth of the bottle body.

Further, the main shell comprises a left shell, a right shell matching with the left shell, a plurality of buckles are arranged at one side of the right shell, and fastening positions matching with the buckles are arranged at one side of the right shell.

Further, assembly grooves matching with the heating body fixing seat are arranged in the left shell and the right shell.

Further, the fragrance emitting area corresponds to the heating body, and the fragrance emitting area is composed of a plurality of fragrance emitting holes.

Further, the rotary plug socket comprises a circular socket main body and a plug sheet installed on the socket main body, one end of the plug sheet is connected with a power receiving sheet, which is in corresponding contact with the conductive copper sheet, and the power receiving sheet is arc-shaped and embedded on the end surface of the socket main body; the side of the socket main body is provided with an annular groove.

Further, one end of the conductive copper sheet is provided with a U-shaped clamping opening matching with the PCB assembly, and the other end is provided with an elastic contact sheet corresponding and matching with the power receiving sheet.

Further, the left and right shells are provided with circular gaps matching with the socket main body, flanges matching the annular grooves are arranged in the circular gaps; and limiting blocks are arranged in the annular grooves.

Further, the plug sheet is set as a national standard plug, a European standard plug, a US standard plug or a British standard plug.

Further, the heating body is a Positive Temperature Coefficient (PTC) heating body, and the PTC heating body is sleeved outside the cotton bar.

Advantages of the Invention

1. By adopting the miniature aromatherapy diffuser disclosed by the invention and providing a rotary plug socket on the main shell, the rotary plug socket can avoid the problem of different directions of the socket, and can effectively maintain the horizontal insertion of the product, so the perfume in the bottle body is prevented from flowing out; the conductive copper sheet is arranged in the main shell, and two ends of the conductive copper sheet are respectively connected with the rotary plug socket and the PCB assembly, and at the same time, the electrodes at the both sides of the heating body are also in contact with the PCB assembly by a connection method, the traditional way of using wires is replaced, the automatic assembly is easy to realize, and the productivity is improved greatly.

2. The main shell is formed by assembling the left shell and the right shell correspondingly, and the left shell and the right shell are fixed by fastening, the assembly efficiency is high, few parts are required, the automatic production is easy, compared with the similar products on the market, the problems of low assembly efficiency and poor automatic production are solved.

3. During the process of assembling the left shell and the right shell, the assembly of the rotary plug socket can be realized, and at the same time, after assembled, the rotary plug socket can make good contact with the conductive copper sheet to realize the connection of the circuit; the connection of the circuit can be realized without other complicated operation, and the whole efficiency of the assembly is improved greatly.

4. The plug sheet can be arranged correspondingly according to the requirements of different exporting countries to assemble sockets in different countries, and the adaptability of the product is improved.

5. The PTC heating body is suitable for voltages of 110V-240V and constant temperature. The similar products in the market are usually cement resistance. The cement resistance cannot be used for wide voltages, and the voltage change temperature cannot be constant temperature.

DETAILED DESCRIPTION OF THE EMBODIMENTS

Figure 1:
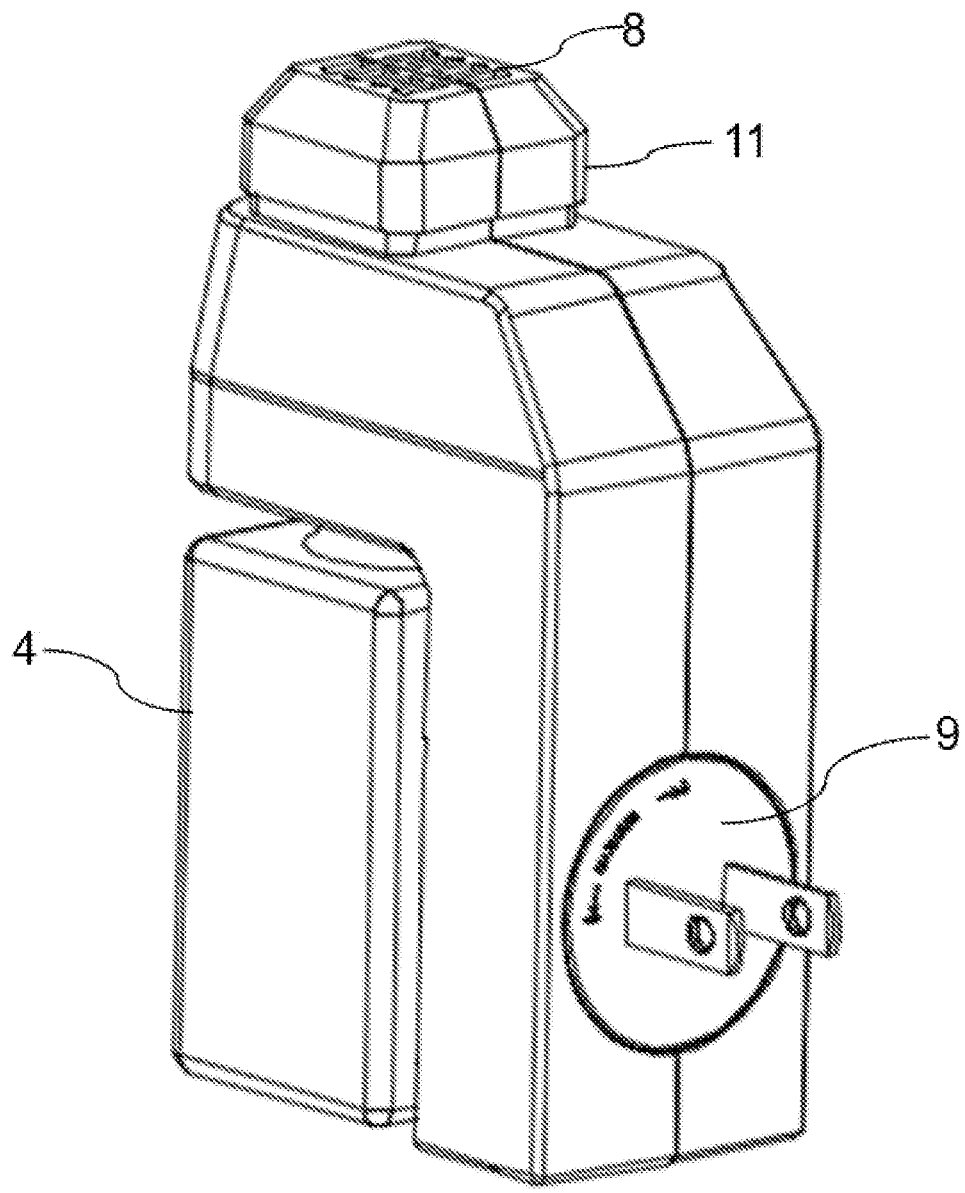
FIG. 1 is a schematic diagram of the whole structure of the front of the miniature aromatherapy diffuser provided by the invention.

To illustrate the purpose, technical scheme and advantages of the embodiment, the technical schemes in the embodiment will be clearly and completely described in combination with the drawings in the embodiment of the invention. Apparently, the described embodiment is a partial embodiment of the invention instead of all embodiments. Generally, the description of the drawing and the components of the embodiment of the invention can be arranged and designed in different configurations.

Therefore, embodiments of the invention described by the drawings herein are to provide selected embodiments of the invention rather than limit the scope of protection. Embodiments developed by technical workers on the basis of the embodiments of the invention without creative efforts are within the scope of protection of the invention.

It should be noted that embodiments included herein as well as their features can be combined as long as they are not mutually exclusive.

It should be noted that similar symbols and letters indicate similar items in the following drawings. Therefore, once an item is defined in one drawing, it will not be further defined and explained in subsequent drawings.

It should be noted that orientations and positions in the description of the embodiments of the invention are based on the drawings, the ordinary placement and arrangement of the devices, the common-sense orientations and positions understood by technical workers of this field. They are merely for the convenience of description. They do not indicate or imply any specific orientation or position that the device or component in discussion must be placed, arranged or operated. In addition, words such as "first" and "second" are used for distinguishing purposes only, and shall not be understood as indicating or implying the relative importance.

In the description of the embodiments of the invention, it should be further noted that the terms "set" and "connect" should be understood broadly. For example, it may refer to a fixed connection, detachable connection, or integrated connection, or otherwise, direct connection or indirect connection through a medium. An ordinary technical worker in the area may make sense of the term according to specific situations. The drawings of the embodiments provide a clear and thorough description of the technical solutions therein. It is obvious the embodiments provided herein are a part of rather than all embodiments of the invention. Components referred to in the description can be designed and arranged in different ways.

Embodiment 1

Figure 2:
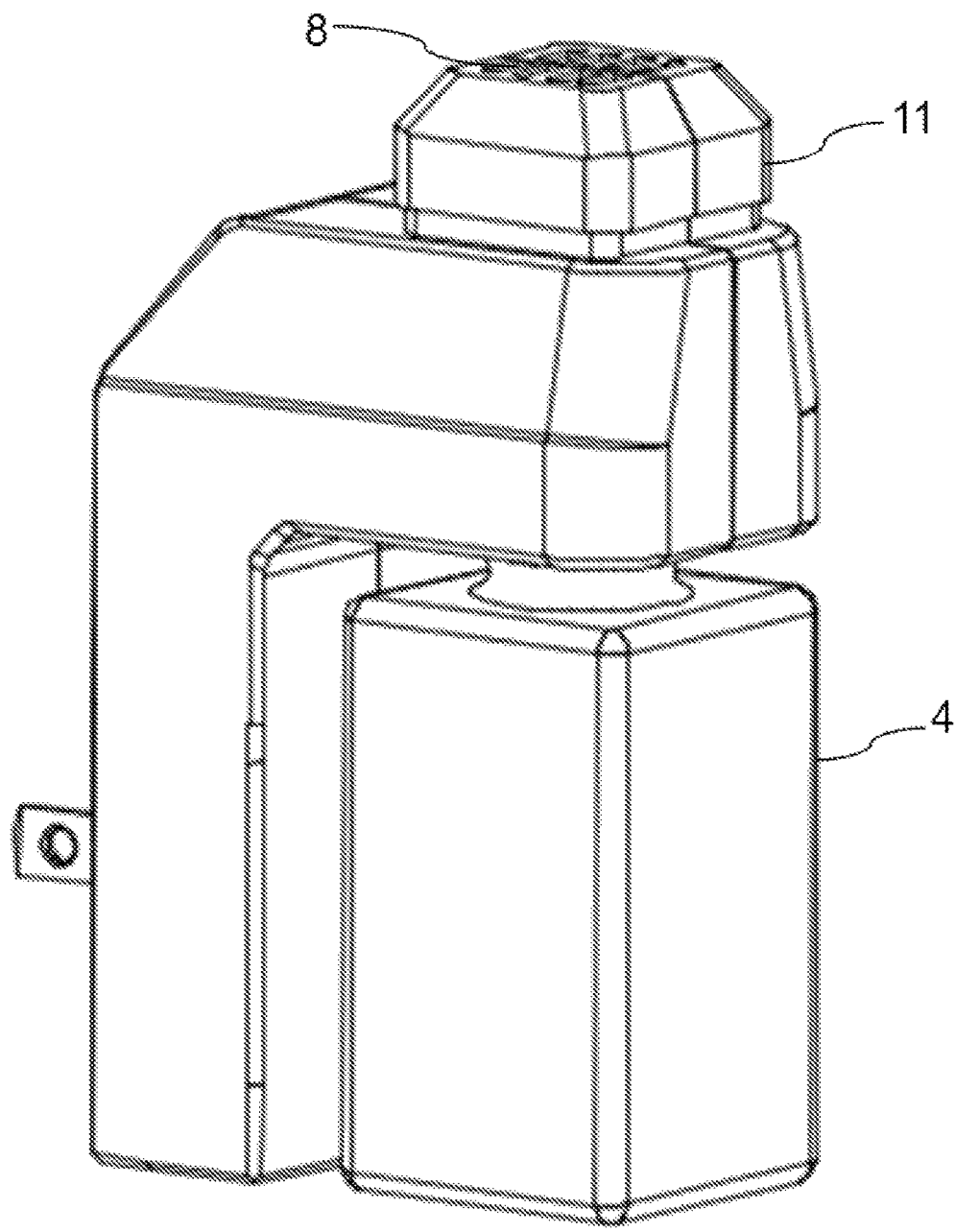
FIG. 2 is a schematic diagram of the whole structure of the back of the miniature aromatherapy diffuser provided by the invention.
Figure 3:
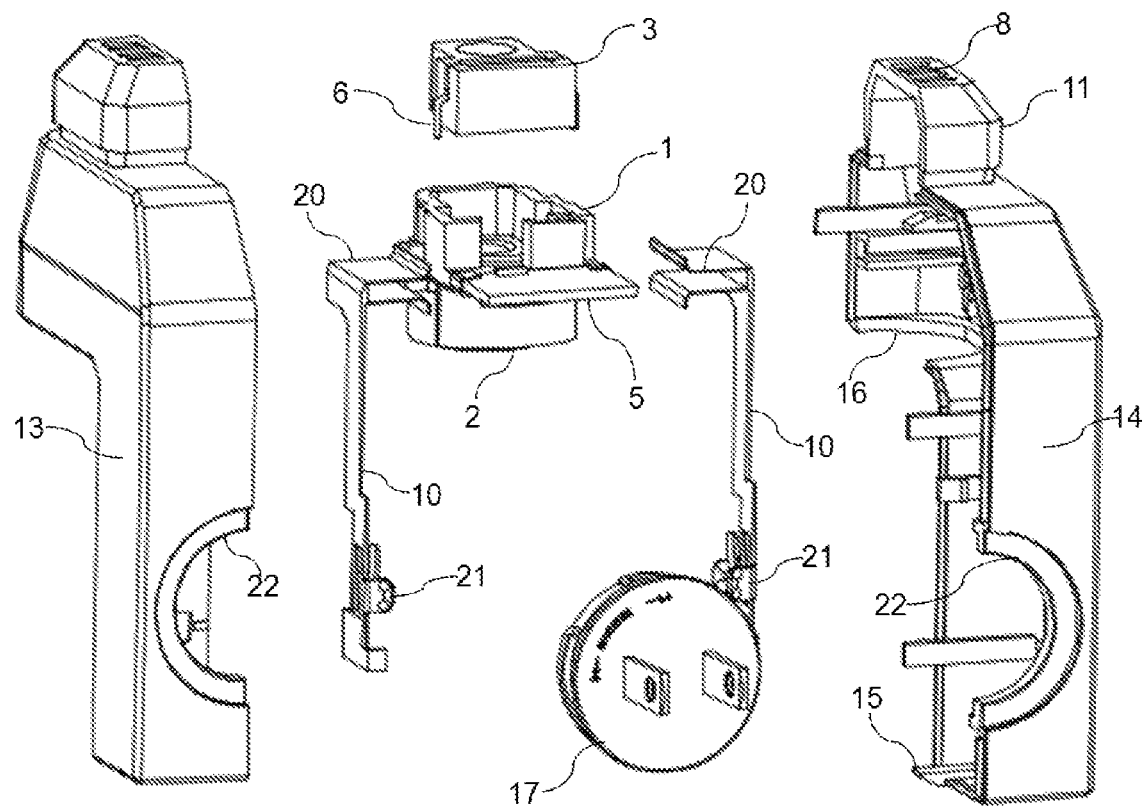
FIG. 3 is a schematic diagram of the disassembly structure of the miniature aromatherapy diffuser provided by the invention.
Figure 4:
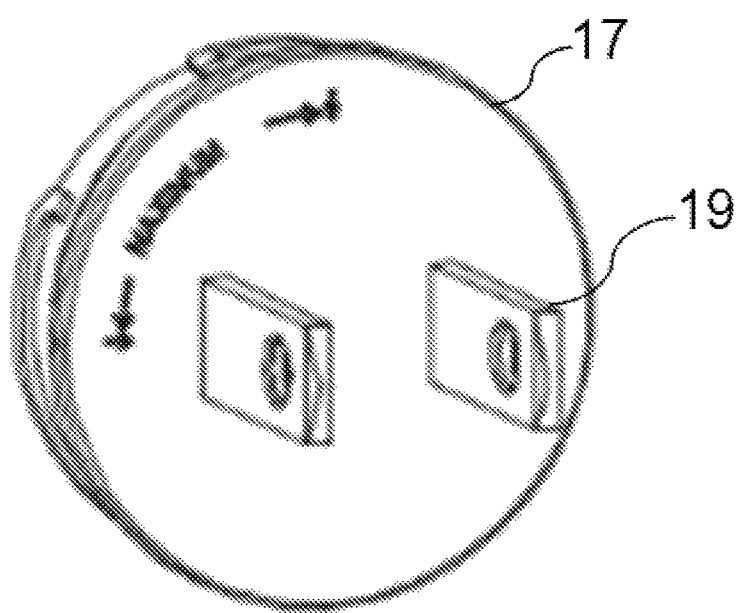
FIG. 4 is a schematic diagram of the whole rotary plug socket in the miniature aromatherapy diffuser provided by the invention.
Figure 5:
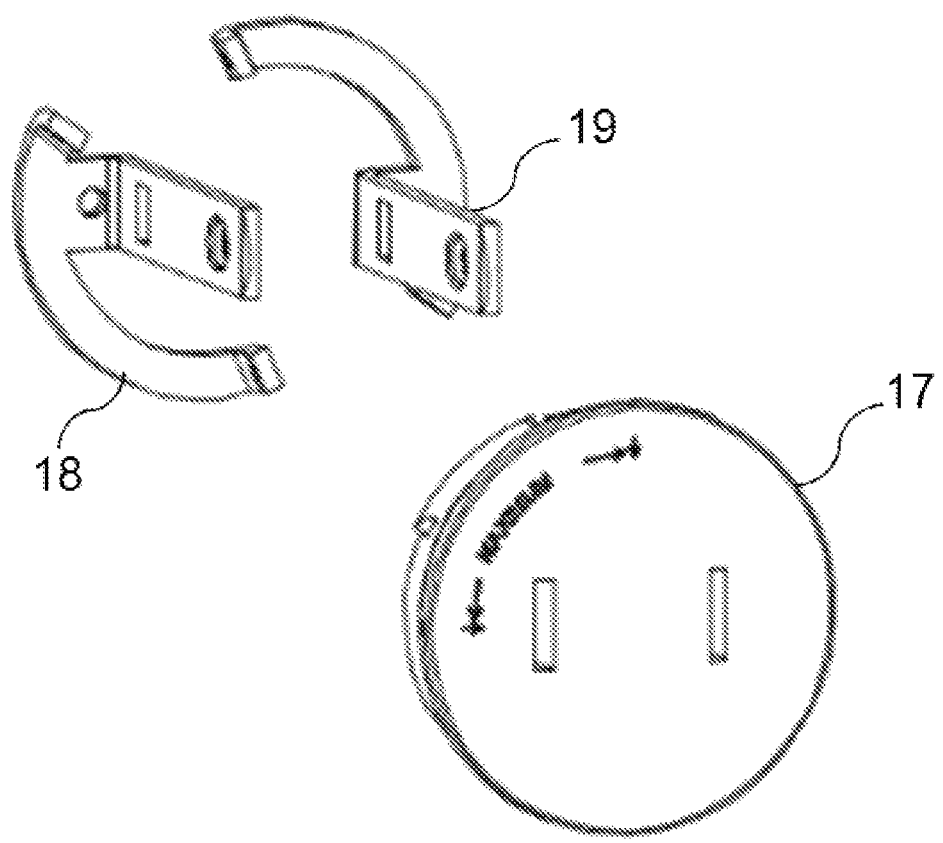
FIG. 5 is a schematic diagram of the disassembly structure of the rotary plug socket in the miniature aromatherapy diffuser provided by the invention.
Figure 6:
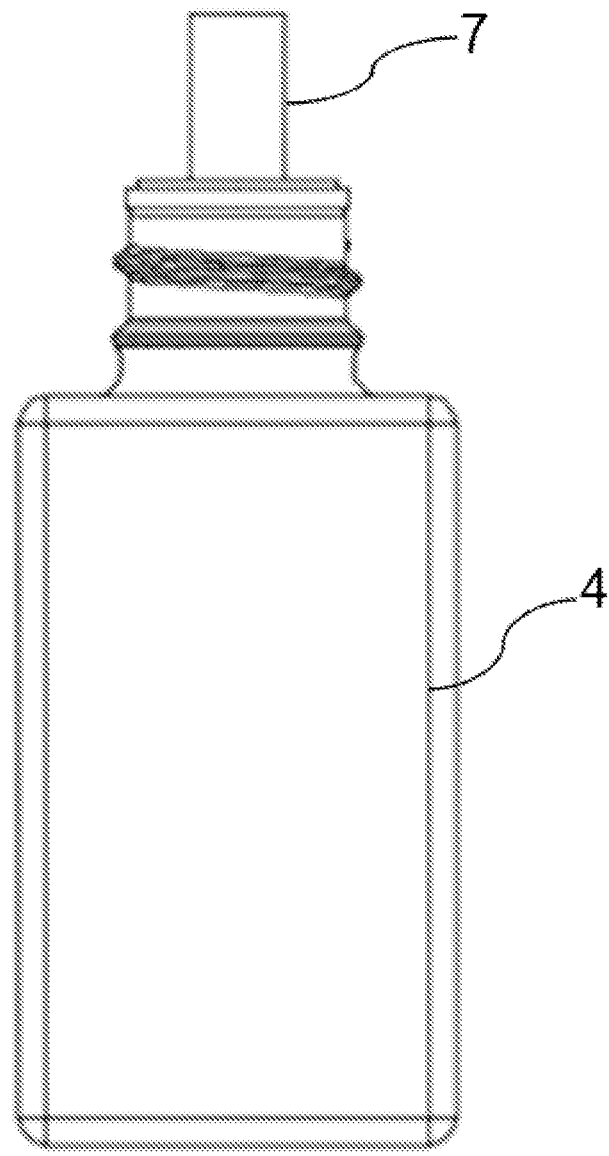
FIG. 6 is a schematic diagram of the whole structure of the perfume bottle assembly in the miniature aromatherapy diffuser provided by the invention.
Figure 7:
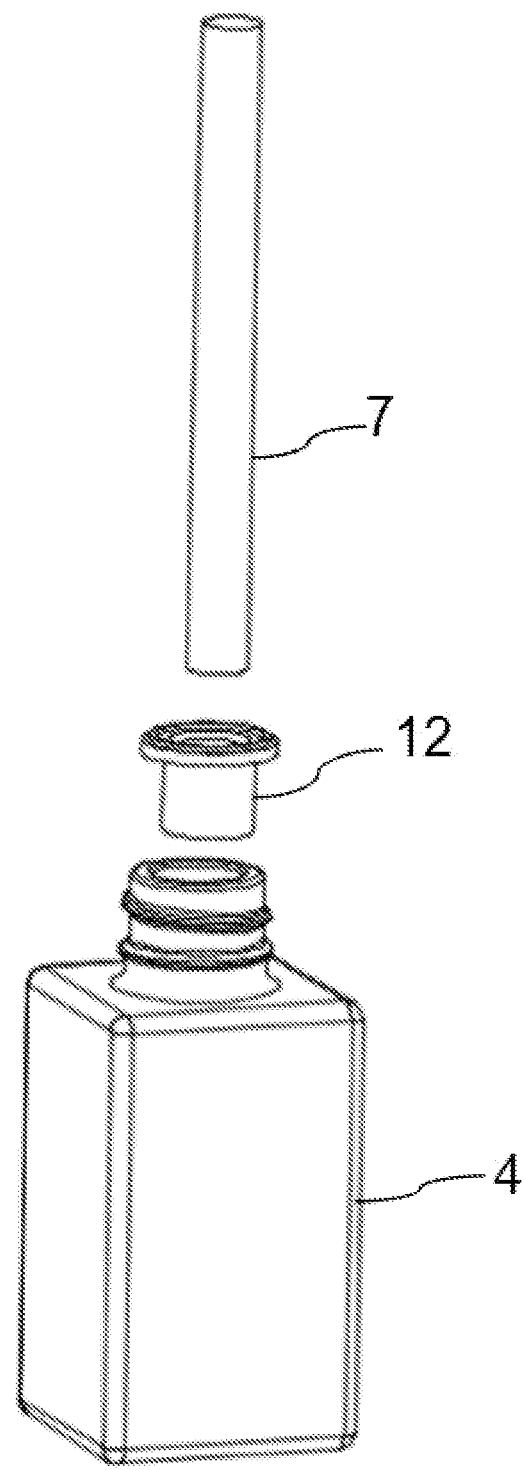
FIG. 7 is a schematic diagram of the disassembly structure of the perfume bottle assembly in the miniature aromatherapy diffuser provided by the invention.

As shown in FIG. 1-FIG. 7, the embodiment provides a miniature aromatherapy diffuser, which comprises a main body and a perfume bottle assembly with hollow structures, and the outline of the main shell is an L-shaped structure, and the perfume bottle assembly is assembled under one side arm of the main shell to assemble a rectangular-like structure, so that the product can be stably placed on the table.

A heating body fixing seat 1 is arranged in the main shell, and the heating body fixing seat 1 is assembled and fixed by a second assembly cavity provided in the main shell, one end of the heating body fixing seat 1 is provided with a connecting cavity 2, the inner wall of the connecting cavity 2 is provided with a connecting thread, which can be connected with the external thread of the bottle mouth of the bottle body 4, and the other end is provided with a first assembly cavity, and the heating body 3 is detachably assembled in the first assembly cavity, and the heating body 3 can be directly inserted or pulled out of the first assembly cavity; when the heating body 3 is inserted into t the first assembly cavity, on the one hand, the heating body 3 can be assembled and fixed; on the other hand, the circuit of the heating body 3 can be connected. The essential oil is placed in the bottle body 4, the essential oil can be immersed in the cotton bar 7, and the essential oil can be changed in various flavors according to personal preference.

A PCB assembly 5 is further arranged on the heating body fixing seat 1. The PCB assembly 5 can effectively control the heating body 3 to perform continuous and stable heating, and both sides of the heating body 3 are provided with electrodes 6 in contact with the PCB assembly 5. Preferably, the PCB assembly 5 comprises a PCB board, the PCB board is fixed on the heating body fixing seat 1, and two power supply contact areas are oppositely arranged on the PCB board, the PCB board is further provided with a positive output terminal and a negative output terminal, a circuit is printed on the PCB to connect the two power contact areas with the positive and negative output terminals respectively, and the positive and negative output terminals are connected with the positive and negative output electrode sheets, the positive and negative output electrode sheets are respectively arranged on the two relative inner walls of the first assembly cavity and the positive and negative output electrode sheets correspond to the electrodes 6 at the two sides of the heating body 3 respectively, so when the heating body 3 is correspondingly assembled in the first assembly cavity, the electrodes 6 at the two sides of the heating body 3 can be in contact with the corresponding positive or negative output electrode sheets to connect the circuit.

The perfume bottle assembly comprises a bottle body 4 and a cotton bar 7, the bottle body 4 is connected with the connecting cavity 2, one end of the cotton bar 7 extends into the bottle body 4 and extends to the bottom of the bottle body 4, the other end extends out of the mouth of the bottle body 4 and extends into the heat body 3, the cotton bar 7 has the following functions of sucking the essential oil into the cotton bar 7 through the cotton bar 7, and then loading the cotton bar 7 containing the essential oil to the center of a ring-shaped heating body 3, the essential oil releases the volatile aroma to the space environment after being heated, and various flavors can be changed according to personal preference.

A fragrance emitting area 8 corresponding to the heating body 3 is arranged on the main shell, and the fragrance emitting area 8 is mainly used for emitting a volatilized fragrance into the air, and the main shell is further provided with a rotary plug socket 9, the rotary plug socket 9 can effectively avoid the problem of different directions of the socket, effectively keep the product being horizontally inserted into the socket, and prevent the perfume in the bottle body 4 from flowing out; a conductive copper sheet 10 is arranged in the main shell, one end of the conductive copper sheet 10 is connected with the rotary plug socket 9 and the other end is connected with the PCB assembly 5. Preferably, in the embodiment, an emitting shell 11 communicating with the inner cavity is provided at the top of the main shell, and the inner cavity of the emitting shell 11 corresponds to the heating body 3 and the end of the emitting shell 11 is provided with the fragrance emitting area 8, and the emitting shell 11 can achieve the function of a chimney to provide a good guiding effect on the heated volatile flavor. The fragrance emitting area 8 is composed of a plurality of fragrance emitting holes, and each fragrance emitting hole is uniformly distributed in the fragrance emitting area 8 so that the heated volatile flavor can be uniformly emitted into the air.

The outer part of the cotton bar 7 is sleeved with a bottle stopper 12, and the bottle stopper 12 is fixed in the mouth of the bottle body 4. The bottle stopper 12 can provide a good seal between the cotton bar 7 and the mouth of the bottle body 4. The essential oil contained in the bottle body 4 can be prevented from being volatilized, and at the same time, the bottle stopper 12 also provides a reliable guarantee for the stable installation of the cotton bar 7.

The main shell comprises a left shell 13 and a right shell 14 matching with the left shell 13. One side of the right shell 14 is provided with a plurality of buckles 15. The number of the buckles 15 can be in adapted setting according to actual conditions. One side of the left shell 13 is provided with fastening positions matching with the buckles 15; when the buckles 15 are inserted into the corresponding fastening positions, the buckling connection between the buckles 15 and the fastening positions can be realized. Certainly, the fastening position can be set on the right shell 14, and the buckles 15 are arranged on left shell 13. Preferably, the left shell 13 and the right shell 14 are one part of the main shell which is cut along a central surface, and the main shell can be assembled by closing the left shell 13 and the right shell 14. In this embodiment, the assembly structure between the left shell 13 and the right shell 14 is arranged to be assembled between the buckle 15 and the fastening position; compared with the connection between the left shell 13 and the right shell 14 through ultrasonic, infrared welding, hot tube hot-melt welding or screw connection, the embodiment has faster assembly efficiency, low assembly cost and assembly difficulty, overcomes the defects that the existing assembly method has low assembly efficiency and is not conducive to automated production.

The left shell 13 and the right shell 14 are respectively provided with assembly grooves matching the heating body fixing seat 1. When the left shell 13 and the right shell 14 are assembled with each other, the two assembly grooves gradually clamp the assembly hump on the side wall of the heating body fixing seat; meanwhile, the first arc gaps 16 are arranged on the left shell 13 and the right shell 14, the first arc gaps 16 are closed to one end of the connecting cavity 2, two first arc gaps 16 form a hole, the mouth of the bottle body 4 is in threaded connection with the connecting cavity 2 by the hole.

The rotary plug socket 9 comprises a circular socket main body 17 and a plug sheet 19 installed on the circular socket main body 17. One end of the plug sheet 19 passes through the circular socket main body 17 and the other end is connected with a power receiving sheet 18; the power receiving sheet 18 is in contact with the conductive copper sheet 10, and the power receiving sheet 18 is arc-shaped and embedded on the end surface of the socket main body 17, the two power receiving sheets 18 are symmetrically distributed on the two sides of the socket main body 17; and the power receiving sheet 18 should have sufficient arc length to realize that after the socket main body 17 is rotated by a certain angle, the power receiving sheet 18 is still in contact with the conductive copper sheet 10; the side of the socket main body is provided with an annular groove, which is a structure capable of freely rotating after the socket main body 17 is assembled.

One end of the conductive copper sheet 10 is provided with a U-shaped clamping opening 20 matching the PCB assembly 5, and the U-shaped clamping opening 20 is clamped on the power contact area of the PCB board of the PCB assembly 5, the connection of the circuit is realized, the other end is provided with an elastic contact sheet 21 correspondingly matching with the power receiving sheet 18. After the rotary plug socket 9 is assembled, the power receiving sheet 18 is embedded in the socket main body 17 and aligns to the elastic contact sheet 21 to ensure good contact between the rotary plug socket 9 and the conductive copper sheet 10 to achieve normal operation of the miniature aromatherapy diffuser.

Second arc gaps matching the socket main body 17 are arranged on the left shell 13 and right shell 14, and flanges 22 matching the annular groove are arranged in the second arc gaps; a first limiting block is arranged in the annular groove, a second limiting block is arranged on the flange 22, when the rotary plug socket 9 rotates relative to the main shell, the first limiting block and the second limiting block act mutually to limit the socket main body 17 to rotate in a certain rotary range, and then the plug sheet 19 arranged on the socket main body is adjusted; during the rotating process, the power receiving sheet 18 on the rotary plug socket 9 can be prevented from moving greatly, and the separation of the power receiving sheet 18 and the elastic contact sheet can be prevented. When the left shell 13 and the right shell 14 are assembled with each other, the flange 22 located in the second arc gap can be fit just in the annular groove, so that the socket main body 17 can rotate relative to the annular groove so as to adjust the relative position of the plug sheet 19, adapt to the sockets in different positions and ensure that the product is always in a horizontal working state.

The plug sheet 19 is set as a national standard plug, and the national standard plug is processed and formed according to the national plug standard to adapt to the universal socket of our country.

The heating body 3 is set as the PTC heating body, and the PTC heating body is sleeved outside the cotton bar 7. The PTC heating body is suitable for voltages of 110V-240V and constant temperature. The similar products in the market are usually cement resistance. The cement resistance cannot be used for wide voltages, and the voltage change temperature cannot be constant temperature.

The miniature aromatherapy diffuser disclosed in this embodiment can greatly improve assembly efficiency, reduce assembly personnel, and realize automated assembly production.

Embodiment 2

On the basis of embodiment 1, in order to further improve the adaptability of the product to different countries, the national standard plug can also be replaced with a European standard plug, a US standard plug or a British standard plug, wherein the European standard plug, the US standard plug or British standard plugs are processed and formed according to the plug standards of the corresponding countries so that the plug sheet 19 can be well adapted in different countries, and will not affect the overall assembly process of the miniature aromatherapy diffuser. In the actual production process, the plugs required by different countries can be assembled according to the requirements of the exporting country.

Preferably, when the plug is replaced by the European standard plug, since the European standard plug is equipped with a grounding wire, since the shell of the product is injection molded by plastic, there is no risk of generating static electricity, and therefore, the conductive copper sheet 10 for connecting the positive and negative electrodes is arranged in the product.

It is obvious that the invention is not limited to the above-mentioned exemplary cases for those skilled in the field. Moreover, they are able to implement the invention in other specific forms without departing from the spirit or basic characteristics of the invention. Therefore, in any way, the embodiments shall be deemed exemplary rather than restrictive. The scope of the invention is defined by the appended claims rather than the descriptions above. Therefore, all changes in the meaning and scope of equivalent elements in the claims are included in the invention. No drawing or mark in the claims shall be construed as limiting the claims involved.

The invention is not limited to the embodiments mentioned above. Anyone inspired by the invention can develop other various forms of products. However, no matter how those products differ with the embodiments in form or structure, as long as their technical solutions fall within the scope of protection of the invention, they shall fall within the scope of protection of the invention.

The invention claimed is:

1. A miniature aromatherapy diffuser, comprising a main shell and a perfume bottle assembly, wherein the main shell and the perfume bottle assembly are hollow structures, a heating body fixing seat is removably arranged in the main shell, a first end of the heating body fixing seat is provided with walls forming a connecting cavity, and a second end of the heating body fixing seat is detachably assembled with a heating body; a PCB assembly is arranged on the heating body fixing seat, and the heating body is provided with electrodes connected to the PCB assembly; the perfume bottle assembly comprises a bottle body and a cotton bar, the bottle body is connected to the walls forming the connecting cavity, a first end of the cotton bar extends into the bottle body, and a second end extends out of the bottle mouth of the bottle body, and extends into the heating body; a fragrance emitting area is arranged on the main shell, and the main shell is also provided with a rotary plug socket; a conductive copper sheet is arranged in the main shell, and a first end of the conductive copper sheet is connected to the rotary plug socket, and a second end of the conductive copper sheet is in contact with the PCB assembly.

2. The miniature aromatherapy diffuser according to claim 1, wherein a bottle stopper is sleeved outside the cotton bar; the bottle stopper is fixed in the mouth of the bottle body.

3. The miniature aromatherapy diffuser according to claim 1, wherein the main shell comprises a left shell, a right shell matching with the left shell, a plurality of buckles are arranged at one side of the right shell, and fastening positions matching with the buckles are arranged at one side of the left shell.

4. The miniature aromatherapy diffuser according to claim 3, wherein assembly grooves matching with the heating body fixing seat are arranged in the left shell and the right shell.

5. The miniature aromatherapy diffuser according to claim 1, wherein the fragrance emitting area is adjacent to the heating body, and the fragrance emitting area is composed of a plurality of fragrance emitting holes.

6. The miniature aromatherapy diffuser according to claim 3, wherein the rotary plug socket comprises a circular socket main body and a plug sheet installed on the circular socket main body, one end of the plug sheet is connected to a power receiving sheet, the power receiving sheet is in corresponding contact with the conductive copper sheet, and the power receiving sheet is arc-shaped and embedded on an end surface of the socket main body; a side of the circular socket main body is provided with an annular groove.

7. The miniature aromatherapy diffuser according to claim 6, wherein the first end of the conductive copper sheet is provided with a U-shaped clamping opening matching with the PCB assembly, and the second end of the conductive copper sheet is provided with an elastic contact sheet corresponding and matching with the power receiving sheet.

8. The miniature aromatherapy diffuser according to claim 6, wherein the left shell and the right shell are provided with arc gaps matching with the circular socket main body, and flanges matching with the annular groove are arranged in the arc gaps; limiting blocks are arranged in the annular groove; and the plug sheet comprises a Chinese standard plug, a European standard plug, a US standard plug or a British standard plug.

9. The miniature aromatherapy diffuser according to claim 1, wherein the heating body is a PTC heating body, and the PTC heating body is sleeved outside the cotton bar.

10. A miniature aromatherapy diffuser according to claim 1, wherein the heating body is disposed within the heating body fixing seat.

11. A miniature aromatherapy diffuser according to claim 1, wherein the main shell comprises a left shell and a right shell matching with the left shell, the left shell and the right shell contacting opposite sides of the heating body fixing seat.

* * * * *